US008852216B2

(12) United States Patent
Cropper et al.

(10) Patent No.: US 8,852,216 B2
(45) Date of Patent: Oct. 7, 2014

(54) TISSUE APPROXIMATION METHODS

(75) Inventors: Michael S. Cropper, Edgewood, KY (US); John P. Measamer, Cincinnati, OH (US); Richard C. Smith, Milford, OH (US); Richard F. Schwemberger, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 952 days.

(21) Appl. No.: 11/690,196

(22) Filed: Mar. 23, 2007

(65) Prior Publication Data

US 2008/0234705 A1    Sep. 25, 2008

(51) Int. Cl.
*A61B 17/08*    (2006.01)
*A61B 17/128*    (2006.01)
*A61B 17/00*    (2006.01)
*A61B 17/122*    (2006.01)

(52) U.S. Cl.
CPC ..... *A61B 17/128* (2013.01); *A61B 2017/00349* (2013.01); *A61B 17/1285* (2013.01); *A61B 2017/00827* (2013.01); *A61B 17/1227* (2013.01)
USPC .......................... 606/157; 606/142; 606/215

(58) Field of Classification Search
USPC ................. 606/139, 151, 155, 157, 158, 142, 606/219–221
See application file for complete search history.

(56) References Cited

U.S. PATENT DOCUMENTS

| 1,343,289 | A | 6/1920 | Suchy |
|---|---|---|---|
| 1,548,250 | A | 8/1925 | Bobner |
| 2,104,885 | A | 1/1938 | robbins |
| 2,199,025 | A | 4/1940 | Conn |
| 3,216,424 | A | 11/1965 | William |
| 3,399,432 | A | 9/1968 | Merser |
| 3,470,875 | A | 10/1969 | Johnson |
| 3,551,987 | A | 1/1971 | Wilkinson |
| 3,636,594 | A | 1/1972 | Faivre et al. |
| 3,638,653 | A | 2/1972 | Berry |
| 3,734,375 | A | 5/1973 | Bone et al. |

(Continued)

FOREIGN PATENT DOCUMENTS

| EP | 0480428 | 4/1992 |
|---|---|---|
| EP | 0576265 A2 | 12/1993 |

(Continued)

OTHER PUBLICATIONS

Feb. 17, 2009, Office Action for U.S. Appl. No. 10/819,996.

(Continued)

*Primary Examiner* — Melanie Tyson
*Assistant Examiner* — Todd J Scherbel
(74) *Attorney, Agent, or Firm* — Mintz Levin Cohn Ferris Glovsky and Popeo, P.C.

(57) ABSTRACT

Methods and devices for approximating tissue are disclosed. The methods and devices utilize a device for applying an implantable tissue fastener and a variety of implantable tissue fasteners. The tissue-fastening device can be delivered endoscopically and can be adapted to function along side or in conjunction with a flexible endoscope. In general, the device can include a flexible shaft having an implantable tissue fastener applier disposed at a distal end of the shaft and a handle for operating the implantable tissue fastener applier disposed at a proximal end of the shaft. A variety of self-deploying implantable tissue fasteners can be used with the tissue fastener applier device.

24 Claims, 10 Drawing Sheets

(56) References Cited

U.S. PATENT DOCUMENTS

| | | |
|---|---|---|
| 3,749,085 A | 7/1973 | Willson et al. |
| 3,842,840 A | 10/1974 | Schweizer |
| 3,875,648 A | 4/1975 | Bone |
| 3,900,925 A | 8/1975 | La Torraca |
| 3,901,244 A | 8/1975 | Schweizer |
| 3,933,291 A | 1/1976 | Stephenson |
| 3,946,740 A | 3/1976 | Bassett |
| 4,006,747 A | 2/1977 | Kronenthal et al. |
| 4,014,492 A | 3/1977 | Rothfuss |
| 4,043,504 A | 8/1977 | Hueil et al. |
| 4,144,890 A | 3/1979 | Hess |
| 4,164,225 A | 8/1979 | Johnson et al. |
| 4,168,703 A | 9/1979 | Kenigsberg |
| 4,177,818 A | 12/1979 | De Pedro |
| 4,210,148 A | 7/1980 | Stivala |
| 4,229,930 A | 10/1980 | Ostermaier |
| 4,235,238 A | 11/1980 | Ogiu et al. |
| 4,265,226 A | 5/1981 | Cassimally |
| 4,375,866 A | 3/1983 | Giersch et al. |
| 4,399,810 A | 8/1983 | Samuels et al. |
| 4,407,286 A | 10/1983 | Noiles et al. |
| 4,448,194 A | 5/1984 | DiGiovanni et al. |
| 4,471,781 A | 9/1984 | Di Giovanni et al. |
| 4,500,024 A | 2/1985 | DiGiovanni et al. |
| 4,506,670 A | 3/1985 | Crossley |
| 4,573,469 A | 3/1986 | Golden et al. |
| 4,585,153 A | 4/1986 | Failla et al. |
| 4,586,502 A | 5/1986 | Bedi et al. |
| 4,591,085 A | 5/1986 | Di Giovanni |
| 4,605,004 A | 8/1986 | Di Giovanni et al. |
| 4,606,345 A | 8/1986 | Dorband et al. |
| 4,607,638 A | 8/1986 | Crainich et al. |
| 4,627,437 A | 12/1986 | Bedi et al. |
| 4,635,637 A | 1/1987 | Schreiber |
| 4,649,938 A | 3/1987 | McArthur |
| 4,653,496 A | 3/1987 | Bundy et al. |
| 4,665,906 A | 5/1987 | Jervis |
| 4,669,473 A | 6/1987 | Richards et al. |
| 4,696,300 A | 9/1987 | Anderson |
| 4,705,040 A | 11/1987 | Mueller et al. |
| 4,724,840 A | 2/1988 | McVay et al. |
| 4,736,746 A | 4/1988 | Anderson |
| 4,741,336 A | 5/1988 | Failla et al. |
| 4,753,469 A | 6/1988 | Hiscott et al. |
| 4,809,695 A | 3/1989 | Gwathmey et al. |
| 4,841,888 A | 6/1989 | Mills et al. |
| 4,862,359 A | 8/1989 | Trivedi et al. |
| 4,880,015 A | 11/1989 | Nierman |
| 4,887,612 A | 12/1989 | Esser et al. |
| 4,890,615 A | 1/1990 | Caspari et al. |
| 4,935,027 A | 6/1990 | Yoon |
| 4,982,727 A | 1/1991 | Sato |
| 5,015,249 A | 5/1991 | Nakao et al. |
| 5,037,021 A | 8/1991 | Mills et al. |
| 5,037,433 A | 8/1991 | Wilk et al. |
| 5,040,715 A | 8/1991 | Green et al. |
| 5,067,957 A | 11/1991 | Jervis |
| 5,076,285 A | 12/1991 | Hess et al. |
| 5,080,663 A | 1/1992 | Mills et al. |
| 5,088,979 A | 2/1992 | Filipi et al. |
| 5,147,373 A | 9/1992 | Ferzli |
| 5,174,487 A | 12/1992 | Rothfuss et al. |
| 5,190,546 A | 3/1993 | Jervis |
| 5,219,359 A | 6/1993 | McQuilkin et al. |
| 5,222,963 A | 6/1993 | Brinkerhoff et al. |
| 5,230,344 A | 7/1993 | Ozdamar et al. |
| 5,254,126 A | 10/1993 | Filipi et al. |
| 5,289,963 A | 3/1994 | McGarry et al. |
| 5,290,296 A | 3/1994 | Phillips |
| 5,309,923 A | 5/1994 | Leuchter et al. |
| 5,318,589 A | 6/1994 | Lichtman |
| 5,324,325 A | 6/1994 | Moaddeb |
| 5,331,969 A | 7/1994 | Silberstein |
| 5,336,263 A | 8/1994 | Ersek et al. |
| 5,346,504 A | 9/1994 | Ortiz et al. |
| 5,350,391 A | 9/1994 | Iacovelli |
| 5,354,311 A | 10/1994 | Kambin et al. |
| 5,356,416 A | 10/1994 | Chu et al. |
| 5,358,508 A | 10/1994 | Cobb et al. |
| 5,364,408 A | 11/1994 | Gordon |
| 5,376,095 A | 12/1994 | Ortiz |
| 5,381,943 A | 1/1995 | Allen et al. |
| 5,383,260 A | 1/1995 | Deschenes et al. |
| 5,389,098 A | 2/1995 | Tsuruta et al. |
| D356,154 S | 3/1995 | Ferragamo |
| 5,395,030 A | 3/1995 | Kuramoto et al. |
| 5,395,367 A | 3/1995 | Wilk |
| 5,403,326 A | 4/1995 | Harrison et al. |
| 5,405,344 A | 4/1995 | Williamson et al. |
| 5,433,721 A | 7/1995 | Hooven et al. |
| 5,437,266 A | 8/1995 | McPherson et al. |
| 5,441,507 A | 8/1995 | Wilk |
| 5,447,512 A | 9/1995 | Wilson et al. |
| 5,451,406 A | 9/1995 | Lawin et al. |
| 5,464,426 A | 11/1995 | Bonutti |
| 5,465,894 A | 11/1995 | Clark et al. |
| 5,470,337 A | 11/1995 | Moss |
| 5,474,057 A | 12/1995 | Makower et al. |
| 5,485,952 A | 1/1996 | Fontayne |
| 5,486,189 A | 1/1996 | Mudry et al. |
| 5,496,331 A | 3/1996 | Xu et al. |
| 5,522,820 A | 6/1996 | Caspari et al. |
| 5,528,334 A | 6/1996 | Lee |
| 5,538,008 A | 7/1996 | Crowe |
| 5,549,618 A | 8/1996 | Fleenor et al. |
| 5,558,665 A | 9/1996 | Kieturakis |
| 5,571,090 A | 11/1996 | Sherts |
| 5,571,116 A | 11/1996 | Bolanos et al. |
| 5,573,496 A | 11/1996 | McPherson et al. |
| 5,581,943 A | 12/1996 | Deren et al. |
| 5,588,581 A | 12/1996 | Conlon et al. |
| 5,597,378 A | 1/1997 | Jervis |
| 5,613,499 A | 3/1997 | Palmer et al. |
| 5,624,453 A | 4/1997 | Ahmed |
| 5,626,613 A | 5/1997 | Schmieding |
| 5,642,552 A | 7/1997 | Wang |
| 5,645,552 A | 7/1997 | Sherts |
| 5,662,683 A | 9/1997 | Kay |
| 5,665,096 A | 9/1997 | Yoon |
| 5,671,507 A | 9/1997 | Deschenes et al. |
| 5,674,230 A | 10/1997 | Tovey et al. |
| 5,676,674 A | 10/1997 | Bolanos et al. |
| 5,697,940 A | 12/1997 | Chu et al. |
| 5,699,808 A | 12/1997 | John |
| 5,700,273 A | 12/1997 | Buelna et al. |
| 5,722,421 A | 3/1998 | Francese et al. |
| 5,725,524 A | 3/1998 | Mulier et al. |
| 5,728,109 A | 3/1998 | Schulze et al. |
| 5,735,861 A | 4/1998 | Peifer et al. |
| 5,741,280 A | 4/1998 | Fleenor |
| 5,749,898 A | 5/1998 | Schulze et al. |
| 5,787,897 A | 8/1998 | Kieturakis |
| 5,788,138 A | 8/1998 | Deschenes et al. |
| 5,792,153 A | 8/1998 | Swain et al. |
| 5,792,478 A | 8/1998 | Lawin et al. |
| 5,794,948 A | 8/1998 | Schmitt et al. |
| 5,797,927 A | 8/1998 | Yoon |
| 5,810,855 A | 9/1998 | Rayburn et al. |
| 5,810,882 A | 9/1998 | Bolduc et al. |
| 5,814,054 A | 9/1998 | Kortenbach et al. |
| 5,820,630 A | 10/1998 | Lind |
| 5,826,776 A | 10/1998 | Schulze et al. |
| 5,845,645 A | 12/1998 | Bonutti |
| 5,846,254 A | 12/1998 | Schulze et al. |
| 5,853,409 A | 12/1998 | Swanson et al. |
| 5,855,311 A | 1/1999 | Hamblin et al. |
| 5,887,594 A | 3/1999 | LoCicero, III |
| 5,893,592 A | 4/1999 | Schulze et al. |
| 5,897,562 A | 4/1999 | Bolanos et al. |
| 5,899,915 A | 5/1999 | Saadat |
| 5,901,895 A | 5/1999 | Heaton et al. |
| 5,947,983 A | 9/1999 | Solar et al. |
| 5,954,731 A | 9/1999 | Yoon |
| 5,958,444 A | 9/1999 | Wallace et al. |

(56) References Cited

U.S. PATENT DOCUMENTS

| | | |
|---|---|---|
| 5,984,932 A | 11/1999 | Yoon |
| 5,993,466 A | 11/1999 | Yoon |
| 6,009,877 A | 1/2000 | Edwards |
| 6,051,003 A | 4/2000 | Chu et al. |
| 6,059,719 A | 5/2000 | Yamamoto et al. |
| 6,059,798 A | 5/2000 | Tolkoff |
| 6,067,990 A | 5/2000 | Kieturakis |
| 6,083,202 A | 7/2000 | Smith |
| 6,086,600 A | 7/2000 | Kortenbach |
| 6,086,603 A | 7/2000 | Termin et al. |
| 6,098,629 A | 8/2000 | Johnson et al. |
| 6,102,887 A | 8/2000 | Altman |
| 6,113,609 A | 9/2000 | Adams |
| 6,129,761 A | 10/2000 | Hubbell |
| RE36,974 E | 11/2000 | Bonutti |
| 6,152,935 A | 11/2000 | Kammerer et al. |
| 6,159,146 A | 12/2000 | El Gazayerli |
| 6,179,840 B1 | 1/2001 | Bowman |
| 6,221,084 B1 | 4/2001 | Fleenor |
| 6,238,335 B1 | 5/2001 | Silverman et al. |
| 6,254,642 B1 | 7/2001 | Taylor |
| 6,258,064 B1 | 7/2001 | Smith et al. |
| 6,267,285 B1 | 7/2001 | Raymond et al. |
| 6,312,437 B1 | 11/2001 | Kortenbach |
| 6,312,448 B1 | 11/2001 | Bonutti |
| 6,315,184 B1 | 11/2001 | Whitman |
| 6,325,503 B1 | 12/2001 | McCue, Jr. et al. |
| 6,352,503 B1 | 3/2002 | Matsui et al. |
| 6,387,104 B1 | 5/2002 | Pugsley, Jr. et al. |
| 6,443,973 B1 | 9/2002 | Whitman |
| 6,454,778 B2 | 9/2002 | Kortenbach |
| 6,461,366 B1 | 10/2002 | Seguin |
| 6,478,210 B2 | 11/2002 | Adams et al. |
| 6,494,888 B1 | 12/2002 | Laufer et al. |
| 6,506,196 B1 | 1/2003 | Laufer |
| 6,540,789 B1 | 4/2003 | Silverman et al. |
| 6,544,291 B2 | 4/2003 | Taylor |
| 6,544,503 B1 | 4/2003 | Vanderhoff et al. |
| 6,547,776 B1 | 4/2003 | Gaiser et al. |
| 6,548,501 B2 | 4/2003 | Hakkinen |
| 6,548,518 B2 | 4/2003 | Rubin et al. |
| 6,551,315 B2 | 4/2003 | Kortenbach et al. |
| 6,551,328 B2 | 4/2003 | Kortenbach |
| 6,552,045 B2 | 4/2003 | Rubin et al. |
| 6,552,046 B2 | 4/2003 | Druzgala et al. |
| 6,552,047 B2 | 4/2003 | Garvey et al. |
| 6,558,400 B2 | 5/2003 | Deem et al. |
| 6,558,429 B2 | 5/2003 | Taylor |
| 6,559,165 B1 | 5/2003 | Rubin et al. |
| 6,562,034 B2 | 5/2003 | Edwards et al. |
| 6,562,795 B2 | 5/2003 | Ashley et al. |
| 6,569,085 B2 | 5/2003 | Kortenbach et al. |
| 6,569,105 B1 | 5/2003 | Kortenbach et al. |
| 6,572,626 B1 | 6/2003 | Knodel et al. |
| 6,575,971 B2 | 6/2003 | Hauck et al. |
| 6,579,301 B1 | 6/2003 | Bales et al. |
| 6,589,238 B2 | 7/2003 | Edwards et al. |
| 6,591,137 B1 | 7/2003 | Fischell et al. |
| 6,591,838 B2 | 7/2003 | Durgin |
| 6,592,596 B1 | 7/2003 | Geitz |
| 6,592,609 B1 | 7/2003 | Bonutti |
| 6,595,909 B2 | 7/2003 | Silverman et al. |
| 6,595,910 B2 | 7/2003 | Silverman et al. |
| 6,604,004 B1 | 8/2003 | Zelickson et al. |
| 6,604,528 B1 | 8/2003 | Duncan |
| 6,605,078 B2 | 8/2003 | Adams |
| 6,609,140 B1 | 8/2003 | Greene |
| 6,613,047 B2 | 9/2003 | Edwards |
| 6,632,227 B2 | 10/2003 | Adams |
| 6,645,201 B1 | 11/2003 | Utley et al. |
| 6,652,545 B2 | 11/2003 | Shipp et al. |
| 6,660,301 B1 | 12/2003 | Vogel et al. |
| 6,663,639 B1 | 12/2003 | Laufer et al. |
| 6,666,848 B2 | 12/2003 | Stone |
| 6,669,713 B2 | 12/2003 | Adams |
| 6,673,058 B2 | 1/2004 | Snow |
| 6,673,070 B2 | 1/2004 | Edwards et al. |
| 6,692,507 B2 | 2/2004 | Pugsley et al. |
| 6,695,764 B2 | 2/2004 | Silverman et al. |
| 6,695,866 B1 | 2/2004 | Kuehn et al. |
| 6,699,243 B2 | 3/2004 | West et al. |
| 6,712,074 B2 | 3/2004 | Edwards et al. |
| 6,712,814 B2 | 3/2004 | Edwards et al. |
| 6,716,226 B2 | 4/2004 | Sixto, Jr. et al. |
| 6,716,233 B1 | 4/2004 | Whitman |
| 6,725,866 B2 | 4/2004 | Johnson et al. |
| 6,743,240 B2 | 6/2004 | Smith et al. |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,793,652 B1 | 9/2004 | Whitman et al. |
| 6,808,491 B2 | 10/2004 | Kortenbach et al. |
| 6,821,285 B2 | 11/2004 | Laufer et al. |
| 6,824,548 B2 | 11/2004 | Smith et al. |
| 6,835,200 B2 * | 12/2004 | Laufer et al. .................. 606/153 |
| 6,843,403 B2 | 1/2005 | Whitman |
| 6,843,794 B2 | 1/2005 | Sixto, Jr. et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,916,332 B2 | 7/2005 | Adams |
| 6,926,722 B2 | 8/2005 | Geitz |
| 6,945,979 B2 | 9/2005 | Kortenbach et al. |
| 6,971,395 B2 | 12/2005 | Edwards et al. |
| 6,981,941 B2 | 1/2006 | Whitman et al. |
| 6,986,737 B2 | 1/2006 | Suzuki et al. |
| 7,032,798 B2 | 4/2006 | Whitman et al. |
| 7,033,370 B2 | 4/2006 | Gordon et al. |
| 7,066,944 B2 | 6/2006 | Laufer et al. |
| 7,077,856 B2 | 7/2006 | Whitman |
| 7,087,073 B2 | 8/2006 | Bonutti |
| 7,153,314 B2 | 12/2006 | Laufer et al. |
| 7,552,853 B2 * | 6/2009 | Mas et al. .................. 227/175.1 |
| 7,758,596 B2 | 7/2010 | Oz et al. |
| 2001/0049537 A1 | 12/2001 | Kortenbach |
| 2001/0056282 A1 | 12/2001 | Sonnenschein et al. |
| 2002/0010418 A1 | 1/2002 | Lary et al. |
| 2002/0022851 A1 | 2/2002 | Kalloo et al. |
| 2002/0063143 A1 | 5/2002 | Adams et al. |
| 2002/0068945 A1 | 6/2002 | Sixto et al. |
| 2002/0068946 A1 | 6/2002 | Kortenbach et al. |
| 2002/0078967 A1 | 6/2002 | Sixto et al. |
| 2002/0082621 A1 | 6/2002 | Schurr et al. |
| 2002/0138086 A1 | 9/2002 | Sixto et al. |
| 2002/0169459 A1 * | 11/2002 | Porat .................. 606/120 |
| 2002/0173786 A1 | 11/2002 | Kortenbach et al. |
| 2002/0193816 A1 | 12/2002 | Laufer et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2002/0198549 A1 | 12/2002 | Sixto et al. |
| 2003/0019905 A1 | 1/2003 | Adams et al. |
| 2003/0036679 A1 | 2/2003 | Kortenbach et al. |
| 2003/0065340 A1 | 4/2003 | Geitz |
| 2003/0065359 A1 | 4/2003 | Weller et al. |
| 2003/0068326 A1 | 4/2003 | Gevas et al. |
| 2003/0069280 A1 | 4/2003 | Koch et al. |
| 2003/0069646 A1 | 4/2003 | Stinson |
| 2003/0083241 A1 | 5/2003 | Young |
| 2003/0086968 A1 | 5/2003 | Gray |
| 2003/0092699 A1 | 5/2003 | Uchida et al. |
| 2003/0130560 A1 | 7/2003 | Suzuki et al. |
| 2003/0130561 A1 | 7/2003 | Suzuki et al. |
| 2003/0135206 A1 | 7/2003 | Edwards et al. |
| 2003/0161887 A1 | 8/2003 | Klein |
| 2003/0163029 A1 | 8/2003 | Sonnenschein et al. |
| 2003/0167062 A1 | 9/2003 | Gambale et al. |
| 2003/0171645 A1 | 9/2003 | Silverman et al. |
| 2003/0181929 A1 | 9/2003 | Geitz |
| 2003/0188755 A1 | 10/2003 | Milbocker |

(56) References Cited

U.S. PATENT DOCUMENTS

| | | |
|---|---|---|
| 2003/0191478 A1 | 10/2003 | Kortenbach et al. |
| 2003/0192558 A1 | 10/2003 | Durgin |
| 2003/0192559 A1 | 10/2003 | Durgin |
| 2003/0195387 A1 | 10/2003 | Kortenbach et al. |
| 2003/0195509 A1 | 10/2003 | Edwards et al. |
| 2003/0196670 A1 | 10/2003 | Durgin |
| 2003/0199731 A1 | 10/2003 | Silverman et al. |
| 2003/0208209 A1 | 11/2003 | Gambale et al. |
| 2003/0208211 A1 | 11/2003 | Kortenbach |
| 2003/0216754 A1 | 11/2003 | Kraemer et al. |
| 2003/0220657 A1 | 11/2003 | Adams |
| 2003/0220660 A1 | 11/2003 | Kortenbach et al. |
| 2003/0236535 A1 | 12/2003 | Onuki et al. |
| 2003/0236536 A1 | 12/2003 | Grigoryants et al. |
| 2004/0006336 A1 | 1/2004 | Swanson |
| 2004/0006351 A1 | 1/2004 | Gannoe et al. |
| 2004/0010245 A1 | 1/2004 | Cerier et al. |
| 2004/0037887 A1 | 2/2004 | Bourne et al. |
| 2004/0044364 A1 | 3/2004 | DeVries et al. |
| 2004/0059349 A1 | 3/2004 | Sixto et al. |
| 2004/0059350 A1 | 3/2004 | Gordon et al. |
| 2004/0059354 A1 | 3/2004 | Smith et al. |
| 2004/0059358 A1 | 3/2004 | Kortenbach et al. |
| 2004/0082859 A1 | 4/2004 | Schaer |
| 2004/0082950 A1 | 4/2004 | Edwards et al. |
| 2004/0082963 A1 | 4/2004 | Gannoe et al. |
| 2004/0116948 A1 | 6/2004 | Sixto et al. |
| 2004/0133238 A1 | 7/2004 | Cerier |
| 2004/0147943 A1 | 7/2004 | Kobayashi |
| 2004/0153107 A1 | 8/2004 | Kayan et al. |
| 2004/0162568 A1 | 8/2004 | Saadat et al. |
| 2004/0176783 A1 | 9/2004 | Edoga et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2005/0033320 A1* | 2/2005 | McGuckin et al. ........... 606/139 |
| 2005/0033328 A1 | 2/2005 | Laufer et al. |
| 2005/0216036 A1* | 9/2005 | Nakao ............................ 606/142 |
| 2006/0025789 A1 | 2/2006 | Laufer et al. |
| 2008/0234703 A1* | 9/2008 | Cropper et al. ............... 606/142 |
| 2009/0198254 A1 | 8/2009 | Laufer et al. |

FOREIGN PATENT DOCUMENTS

| | | |
|---|---|---|
| EP | 0593920 | 4/1994 |
| EP | 593920 A1 | 4/1994 |
| EP | 0646356 A2 | 4/1995 |
| EP | 0668058 A1 | 8/1995 |
| EP | 0743044 A1 | 11/1996 |
| EP | 0975263 A1 | 2/2000 |
| FR | 2768324 A1 | 3/1999 |
| GB | 2075829 A | 11/1981 |
| JP | 61122852 A | 6/1986 |
| JP | 1151461 A | 6/1989 |
| JP | 05103241 A | 4/1993 |
| JP | 05323412 A | 12/1993 |
| JP | 08006102 A | 1/1996 |
| JP | 2000254143 A | 9/2000 |
| JP | 2001507972 T | 6/2001 |
| JP | 2003051982 A | 2/2003 |
| JP | 2006311060 A | 11/2006 |
| WO | WO-8911827 A1 | 12/1989 |
| WO | WO-9529635 A1 | 11/1995 |
| WO | WO-9627345 A2 | 9/1996 |
| WO | WO-9803151 A1 | 1/1998 |
| WO | WO-9900059 | 1/1999 |
| WO | WO-9922649 | 5/1999 |
| WO | WO-9960931 | 12/1999 |
| WO | WO-0035529 | 6/2000 |
| WO | WO-0078227 | 12/2000 |
| WO | WO-0078229 | 12/2000 |
| WO | WO-0185034 A1 | 11/2001 |
| WO | WO-0224080 | 3/2002 |
| WO | WO-0228289 A1 | 4/2002 |
| WO | WO-0240081 | 5/2002 |
| WO | WO-0245603 | 6/2002 |
| WO | WO-02076541 | 10/2002 |
| WO | WO-02094341 | 11/2002 |
| WO | WO-02094341 A2 | 11/2002 |
| WO | WO-03000115 | 1/2003 |
| WO | WO-03004087 | 1/2003 |
| WO | WO-03007796 | 1/2003 |
| WO | WO-03015604 | 2/2003 |
| WO | WO-03030782 | 4/2003 |
| WO | WO-03035649 | 5/2003 |
| WO | WO-03037256 | 5/2003 |
| WO | WO-03053253 | 7/2003 |
| WO | WO-03072196 | 9/2003 |
| WO | WO-03082359 A1 | 10/2003 |
| WO | WO-03090633 | 11/2003 |
| WO | WO-03092498 | 11/2003 |
| WO | WO-03092509 | 11/2003 |
| WO | WO-03094800 | 11/2003 |
| WO | WO-03096885 A2 | 11/2003 |
| WO | WO-03098885 | 11/2003 |
| WO | WO-03099137 | 12/2003 |
| WO | WO-03099139 | 12/2003 |
| WO | WO-03099140 | 12/2003 |
| WO | WO-03099376 | 12/2003 |
| WO | WO-03105917 | 12/2003 |
| WO | WO-04000129 | 12/2003 |
| WO | WO-2004004542 | 1/2004 |
| WO | WO-2004004544 | 1/2004 |
| WO | WO-2004006990 | 1/2004 |
| WO | WO-2004019787 | 3/2004 |
| WO | WO-2004019788 | 3/2004 |
| WO | WO-2004021872 | 3/2004 |
| WO | WO-2004021873 | 3/2004 |
| WO | WO-2004021894 | 3/2004 |
| WO | WO-2004026348 | 4/2004 |
| WO | WO-2004026349 | 4/2004 |
| WO | WO-2004026350 | 4/2004 |
| WO | WO-2005086885 | 9/2005 |

OTHER PUBLICATIONS

Feb. 20, 2009, Office Action for U.S. Appl. No. 10/819,957.

Bancewicz et al 'Yield Pressure, Anatomy of the cervix and Gastrooesphageal Reflux' The American Journal of Gastroenterology, vol. 91, No. 3, (1996) pp. 616-617.

Boerema MD 'Hiatus Hernia: Repair by right-sided, subhepatic, anterior gastropexy' Surgery, 65:884-893 (1969).

Carvalho PJPC et al Fibrosis of gastric cardia after endoscopic sclerosis. Mechanism for control of experimental reflux? Am Surg Mar. 1990; 56(3):163-6.

Cecconello, "Esophagogastric Anastomosis with Valvuloplasty: An Experimental Study," *International Surgery*, 67:121-124 (1982).

Collis, M.D., "An Operation for Hiatus Hernia with Short Esophagus " *The Journal of Thoracic Surgery*, 34:768-778 (1957).

Collis, M.D., "Surgical Control of Reflux in Hiatus Hernia," *The American Journal of Surgery*, 115:465-471 (1968).

Contractor QQ et al., Endoscopic esphagitis and gastroesophageal flap valve. J Clin Gastroenterol Apr. 1999; 28 (3):233-7.

Cuschieri, et al., "Multicenter prospective evaluation of laparoscopic antireflux surgery," Surgical Endoscopy, 7:505-510 (1993).

DeMeester, MD et al 'Nissen Fundoplication for Gastroesophageal Reflux Disease' Annals of Surgery 204:9-20 (1986).

Digestive Disease Week, Orange County Convention Center, p. A-802; 314.

Donahue PE et al., Endoscopic sclerosis of the gastric cardia for prevention of experimental gastroesophageal reflux, *Gastrointest. Endosc.* May-Jun. 1990 36(3):253-6.

Donahue, M.D., et al. "Endoscopic Control of Gastro-Esophagel Reflux: Status Report," *World Journal of Surgery*, 16:343-346 (1992).

European Search Report dated Sep. 2, 2004 in EP 04076389.

Eurpoean Search Report mailed Jul. 10, 2007 in EP Application No. 07075291.

(56) References Cited

OTHER PUBLICATIONS

Falk, et al., "Laparoscopic Fundoplication: A preliminary report of the technique and postoperative care," Aust. N.Z. J. Surgery, 62:969-972 (1992).
Hill et al 'Surgery for Peptic Esophageal Stricture' 139-147.
Hill et al 'The Esophagus, Medical and Surgical Management' WB Saunders Co. 135-8 (1988).
Hill LD 'Myths of the esophagus' J Thorac Cardiovasc Surg Jul. (1989)98(1):1-10.
Hill LD and Kozarek RA, The gastroesophageal flap valve, *J. Clin. Gastroenterol* Apr. 1999 28(3): 194-7.
Hill LD et al., Antireflux surgery. A surgeon's look, *Gastroenterol Clin. North Am.*, Sep. 1990 19(3):745-75.
Hill LD et al., The gastroesophageal flap valve: in vitro and vivo observations. Gastrointest Endosc Nov. 1999;44(5):541-7.
Hill LD, Intraoperative measurement of lower esophageal sphincter pressure. J. Thorac Cardiovasc Surg Mar. 1978;75(3):378-82.
Hill LD, Myths of the esophagus, *J. Thorac Cardiovasc. Surg.* Jul. 1989 9S(1):1-10.
Hill MD 'An Effective Operation for Hiatal Hernia: An Eight Year Appraisal' Annals of Surgery (1967) 166:681-692.
Hill, et al., "The Esophagus. Medical and Surgical Management," *WB Saunders Co.*, 135-8 (1998).
Hinder, et al. "The Surgical Option for Gastroesophageal Reflux Disease," Symposium on Gastroesophageal Reflux Disease, *Am. J. Med.* 103: 1445-1485 (1997).
International Search Report dated Oct. 16, 2000.
International Search Report dated Oct. 22, 2003.
Ismail T. et al., Yield pressure, anatomy of the cardia and gastro-oesophageal reflux. Br. J Surg Jul. 1995;82(7):943-7.
Ismail, et al., "Yield Pressure: A New Concept in the Evaluation of Gerd?," *AJG*, 91:616-617 (1996).
Jamieson, et al., "Laparoscopic Nissen Fundoplication," *Annals of Surgery*, 220:137-145 (1994).
Jamieson, et al., "The development of surgery for gastro-oesophageal reflux disease." *Surgery of the Oesophagus*, 233-245 (1988).
Janssen, et al., "Prospective randomized comparison of teres cardiopexy and Nissen fundoplication in the surgical therapy of gastro-oesophageal reflux disease." *Br. J. Surg.*, 80:875-878 (1993).
Japanese Office Action for Application No. 2005-122394 dated May 12, 2009.
Japanese Preliminary Report (Application No. 2004-506665) dated Mar. 31, 2009.
Jennings, et al., "A Novel Endoscopic Transgastric Fundoplication Procedure for Gastroesophageal Reflux: An Initial Animal Evaluation " *Journal of Laparoendoscopic Surgery*, 2:207-213 (1992).
Kadirkamanathan SS et al., An ambulant procine model of acid reflux used to evaluate endoscopic gastroplasty. Gut Jun. 1999;44(6):782-8.
Kadirkamanathan SS et al., Antireflux operations at flexible endoscopy using enodluminal stitching techniques: an experimental study. Gastrointest Endosc Aug. 1996;44(2):133-43.
Kahrilas, "Gastroesophageal Reflux Disease," *JAMA*, 276:983-988 (1996).
Kraemer, MD et al 'Laparascopic Hill repair' Gastrointestinal Endoscopy,vol. 40 No. 2 155-159 (1994).
Little, M.D., "Mechanisms of Action of Antireflux Surgery: Theory and Fact," World Journal of Surgery, 16:320-325 (1992).
Mason et al 'Nissen Fundoplication Prevents Shortening of the Sphincter During Gastric Distention' Arch Surg., 132:719-726 (1997).
Mason RJ et al., A new intraluminal antigastroesphageal reflux procedure in baboons. Gastrointest Endosc Mar. 1997;45(3):283-90.
McGouran RC and Galloway JM, A laser-induced scar at the cardia increases the yield pressure of the lower esophageal sphicter, *Gastrointest. Endosc.* Sep.-Oct. 1990 36(5):439-43.
McGouran RC et al., Does measurement of yield pressure at the cardia during endoscopy provide information on the function of the lower oesophageal sphicter mechanism? Gut Mar. 1998 29(3):275-8.
McGouran RC et al., Is yield pressure at the cardia increased by effective fundoplication? *Gut* Oct. 1998; 30(10): 1309-12.

McKernan, "Laparoscopic repair of gastroesophageal reflux disease," Surgical Endoscopy, 8:851-856 (1994).
Nathanson, et al., "Laparoscopic Ligamentum teres (round ligament) cardiopexy," *Br. J. Surg.*, 78:947-951 (1991).
Nissen, "Eine einfache Operation zur Beeinflussung der Refluxoesophagitis," *Journal Suisee DeMedecine*, 590-592 (1956).
O'Connor KW and Lehman GA, Endoscopic placement of collagen at the lower esophageal sphicter to inhibit gastroesophageal reflux: a pilot study of 10 medically intractable patients. Gastrointest. Endosc. Mar.-Apr. 1998 34(2):106-12.
O'Connor KW et al., An experimental endoscopic technique for reversing gastroesophageal reflux in dogs by injecting inert material in the distal esophagus. *Gastrointest. Endosc.* Oct. 30, 1984(5):275-80.
O'Connor, et al., "Endoscopic placement of collagen at the lower esophageal sphicter to inhibit gastroesophageal reflux: a pilot study of 10 medically intractable patients " *Gastrointestinal Endoscopy*, 34:106-112 (1988).
Pedinielli, "Traitement Chirurgical de la Herinie Hiatale Par La Technique du Collet," *Ann. Chir.*, 18:1461-1474 (1964). (English Abstract).
Polk, et al., "Hiatol Hernia and Esophagitis: A survey of indications for operation and technic and results of fundoplication," *Ann. Surg.*, 173:775-781 (1971).
Rampal, et al., "Technique Chirurgicale, Traitement des hernies hiatales et du reflux aesophagien par la cardio-pexie avec le ligament round de foie," *La Presse Medicale*, 75:617-619 (1967).
Rich, "Simple GERD Treatment Offers New Alternative" (www.medicalpost.com website), Mar. 1999.
Rupp TH and Lehman GA, Endoscopic antireflux techniques. Endoluminal and laparoscopic. *Gastrointest. Endosc. Clin. N. Am.* Apr. 4, 1994(2):353-68.
Shafik A., Intraesophageal Polytef injection for the treatment of reflux esophagitis. *Surg. Endosc.* Mar. 10, 1996(3):329-31.
Singh et al., "Evaluation of the Endoscopic Suturing System in the Treatment of the GERD," Conference Abstract for Plenary Session for Digestive Disease Week, p. 314 & A-802, May 16-19, 1999.
Skinner et al 'Surgical management of esophageal reflux and hiatus hernia' Journal of Thoracic and Cardiovascular Surgery (1967) vol. 53, No. 1 pp. 33-54.
Slim K et al., Intraoperative esophageal manometry and fundoplications: prospective study, World J Surg Jan. 1996;20(1):55-59.
Starling et al 'Assessment of the Angelchik Prosthesis for Treatment of Symptomatic Esophageal Reflux' World J. Surg. 11, 350-355 (1987).
Starling et al., "Treatment of Symptomatic Gastroesophageal Reflux Using the Angelchik™ Prosthesis," *Ann. Surg.* (1982) 686:690.
The Americal journal of gastroenterology, vol. 91, No. 3, 1996, p. 616-617.
Thor KBA et al., Reappraisal of the flap valve mechanism in the gastroesophageal junction. A study of a new valvuloplasty procedure in cadavers. *Acta Chir Scand* Jan. 1987 153(1):25-8.
Tocornal, M.D., et al., A mucosol flap valve mechanism to prevent gastroesophageal reflux and esophagitis, *Surgery*, 64:519-523 (1968).
Wang, et al., "A new anti-flux procedure: cardiac oblique invagination " *Chung Hua Wai Ko Tsa Chih*, Feb. 33 (2) 73-5 (1995). (English Abstract).
Watson, et al., "Comparison of anterior, posterior and total fundoplication using a viscera model," *Diseases of the Esophagus*, 10:110-114 (1997).
Westbrook, et al., "Posterior Surgical Approaches to the Rectum," *Annals of Surgery*, 195:677-685 (1982).
European Office Action dated Apr. 3, 2009 in EP07075291.0.
European Office Action dated Feb. 2, 2010 in EP03 728 882.6.
European Office Action dated Sep. 11, 2009 in EP05 077 998.2.
Moss Tubes advertisement, *Annals of Surgery*, vol. 220, No. 2, Aug. 1994 (2 pages).
Dodds WJ et al. 1982, N Engl J Med 307:1547-52.
European Office Action dated Feb. 11, 2010 in EP03 728 882.6.
Hetzel DJ et al. 1988, Gastroenterology 95:903-12.

(56) References Cited

OTHER PUBLICATIONS

Japanese Office Action for Application No. 2004-131922 dated Jan. 18, 2010 (English translation).
Klinkenberg-Knol EC and Meuwissen SG 1988, Aliment Pharmacol Ther 2:221-7.
Klinkenberg-Knol EC and Meuwissen SG 1989, Digestion 1:47-53.
Lambert R et al. 1993, Gastroenterology 104:1554-7.
Poynter D et al. 1985, Gut 26:1284-95.
Solcia E et al. 1993, Aliment Pharmacol Ther 7(supp. 1):25-8.
Spechler SJ 1992, N Engl J Med 326:786-92.

* cited by examiner

TISSUE APPROXIMATION METHODS

FIELD OF THE INVENTION

The present invention relates to methods and devices for approximating tissue.

BACKGROUND OF THE INVENTION

Gastroesophageal reflux disease (GERD) is a common upper gastrointestinal disorder. GERD is a condition in which acidic contents of the stomach flow inappropriately from the stomach into the esophagus. Chronic irritation of the esophagus leads to inflammation of the esophagus, known as esophagitis. In addition to esophagitis, complications of GERD include Barrett's esophagus, esophageal stricture, intractable vomiting, asthma, chronic bronchitis, and aspiration pneumonia. Pharmacological therapy is available and commonly used. However, this therapy does not address the fundamental problem of stomach content flowing in the inappropriate retrograde and into the esophagus.

Normally, the lower esophageal sphincter (LES) allows food to pass from the esophagus to the stomach, while otherwise remaining closed, thus preventing reflux. Closure of the LES is an active process, requiring a combination of proper mechanics and intact innervation. Additionally, the diaphragm may act on the esophagus normally to keep it closed at the LES. Backflow of gastric contents into the esophagus results when gastric pressure is sufficient to overcome the pressure gradient that normally exists at the gastroesophageal junction (GEJ) or when gravity acting on the contents is sufficient to cause flow, retrograde through the GEJ. This situation arises when the gastric pressure is elevated or when the competence of the LES is comprised. Gastric pressure is elevated in association with eating, bending at the waist, squatting, constriction of the waist by clothing, obesity, pregnancy, partial or complete bowel obstruction, etc. Gravitational effects occur when a patient with this condition becomes recumbent. Incompetence of the LES can be functional or anatomic in origin. Function incompetence is associated with hiatus hernia, denervation, myopathy, scleroderma, and chemical or pharmacological influences (smoking, smooth muscle relaxants, caffeine, fatty foods, and peppermint). Anatomic incompetence is associated with congenital malformation, surgical disruption (myotomy, balloon dilatation or bouginage), neoplasm, etc.

The principal types of operations that address the issues with GERD have included some type of reconstruction of the antireflux barrier, which may include a gastric wrap, as in classic Nissen fundoplication, Toupet fundoplication, a non-gastric wrap, e.g., the Angelchik prothesis, a ligamentum teres cardiopexy, and fixation of a part of the stomach to an immobile structure, e.g., the preaortic fascia, as in the Hill repair or the anterior rectus sheath. Several of these operations also include a crural repair of the esophageal hiatus in the diaphragm.

Other clinical studies have shown that tightening the LES helps reduce GERD. The requirement is to gather tissue from various locations forming a serosa-to-serosa plication, and securing the tissue position until the tissue unites. The resulting tightening in the LES will increase competency in preventing acid reflux.

Typically, these procedures are performed surgically through an open incision or with traditional laparoscopic and laparotomy techniques. Accordingly, a need exists for methods and devices for approximating tissue using an endoscopic approach.

SUMMARY OF THE INVENTION

The present invention generally provides devices and methods for approximating tissue. In one embodiment, a device for applying an implantable tissue fastener is provided having an elongate sheath, a handle that can be disposed at a proximal end of the elongate sheath, and an applier mechanism that can be disposed at a distal end of the elongate sheath and can be adapted to retain a tissue fastener. The elongate sheath can be flexible or it can be rigid. At least one actuator mechanism that can be disposed on the handle for actuating various operations of the device. For example, an actuator mechanism can be operatively associated with the applier mechanism such that actuating the actuator mechanism is effective to release the tissue fastener and thereby apply the tissue fastener to a targeted tissue.

The applier mechanism can have a variety of configurations. For example, in one exemplary embodiment, the applier mechanism can include at least one movable member for releasably retaining a tissue fastener. The at least one movable member can be in the form of a movable jaw that is adapted to open and close and retain the tissue fastener in a tissue grasping condition and a natural condition in the open and closed positions, respectively. An actuator mechanism can be operatively associated with the at least one movable member such that actuating the mechanism is effective to move the at least one movable member. In one embodiment, the actuator mechanism can be a trigger that is disposed on the handle of the device. Applying a force to the trigger can be effective to move the at least one movable member between open and closed positions.

The device can also include a tissue grasping member that is slidably disposed in a longitudinally extending channel formed in the device. Another actuator mechanism can be disposed on the handle and be operatively associated with the tissue grasping member such that actuating the mechanism is effective to slidably move the tissue grasping member with respect to the device.

A variety of implantable tissue fasteners are also provided. In one exemplary embodiment, an implantable tissue fastener is provided having a central body portion, a first anchor arm, and a second anchor arm. The first anchor arm can extend from a first end of the central body portion and can have a terminal end that is opposite the first end of the central body portion. The second anchor arm can extend from a second end of the central body portion and can have a terminal end that is opposite the second end of the central body portion. The terminal ends of the first and second anchor arms can be biased towards each other such that terminal ends are in close proximity with each other when the tissue fastener is in a natural condition.

The central body portion of the tissue fastener can have a variety of configurations. For example, in an exemplary embodiment, the central body portion can include a curved portion. The first and second anchor arms can extend from the curved central body portion, and the terminal ends can overlap to form a circular-shaped fastener when the fastener is in a natural condition. In another embodiment, the first anchor arm can be curved and can extend from the curved central body portion and continue along the same curve. The second anchor arm can be straight and can include a terminal end that extends perpendicular thereto.

In one embodiment, the central body portion can take the form of a spring. In another embodiment, the central body portion can be formed from a super elastic alloy. The central body portion can be part of a unitary structure with the first and second anchor arms or can be a separate element that is coupled to the first and second anchor arms.

A variety of configurations are available for the first and second anchor arms. For example, the first and second anchor arms can be straight or can have an arcuate shape. The terminal ends of the first and second anchor arms can be rounded or blunt or can have tissue piercing points that are adapted to penetrate tissue. In an exemplary embodiment, the piercing points can extend at an angle with respect to an axis of the anchor arm.

In another aspect of the invention, a method for applying a fastener to tissue is provided and can generally include inserting a device for applying an implantable tissue fastener, positioning the device adjacent a targeted tissue, actuating the device to move the tissue fastener from its natural condition to a tissue grasping condition, reconfiguring the targeted tissue, and releasing the tissue fastener to approximate the targeted tissue. In one embodiment, the device can be used in conjunction with an endoscope to facilitate viewing of at least a portion of the method for approximating and can be inserted translumenally through a working channel of the endoscope or through an accessory channel that is mated to the endoscope. In another embodiment, the device can be used in conjunction with a laparoscope and can be inserted through a trocar that extends from an access port. A variety of configurations are available for the approximating device, but the device can generally have at least one movable member that is adapted to retain and release at least one selectively releasable tissue fastener in its natural condition.

Actuating the device to move the tissue fastener from its natural condition to a tissue grasping condition can include moving the at least one movable member from a closed to an open position. The method can also include actuating the device to move the at least one movable member from an open to a closed position to apply a clamping force to a tissue fastener. Reconfiguring the targeted tissue can include manipulating the tissue with a tissue grasping member. In an exemplary embodiment, reconfiguring the targeted tissue can include retracting the tissue to position the tissue adjacent the at least one movable member. Retracting the tissue can be effective to release the tissue fastener. In one embodiment, reconfiguring and applying the fastener to the targeted tissue can be performed using only the device for applying the implantable tissue fastener. Applying the fastener to approximate the targeted tissue can include engaging and applying a force to the targeted tissue with an arcuate portion of the tissue fastener. In another embodiment, applying the fastener to the targeted tissue can include penetrating the tissue with piercing points that are disposed on the tissue fastener. In another aspect of the invention, the steps of actuating the device to move the tissue fastener from its natural condition to a tissue grasping condition, reconfiguring the targeted tissue, and releasing the tissue fastener can be repeated as desired.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
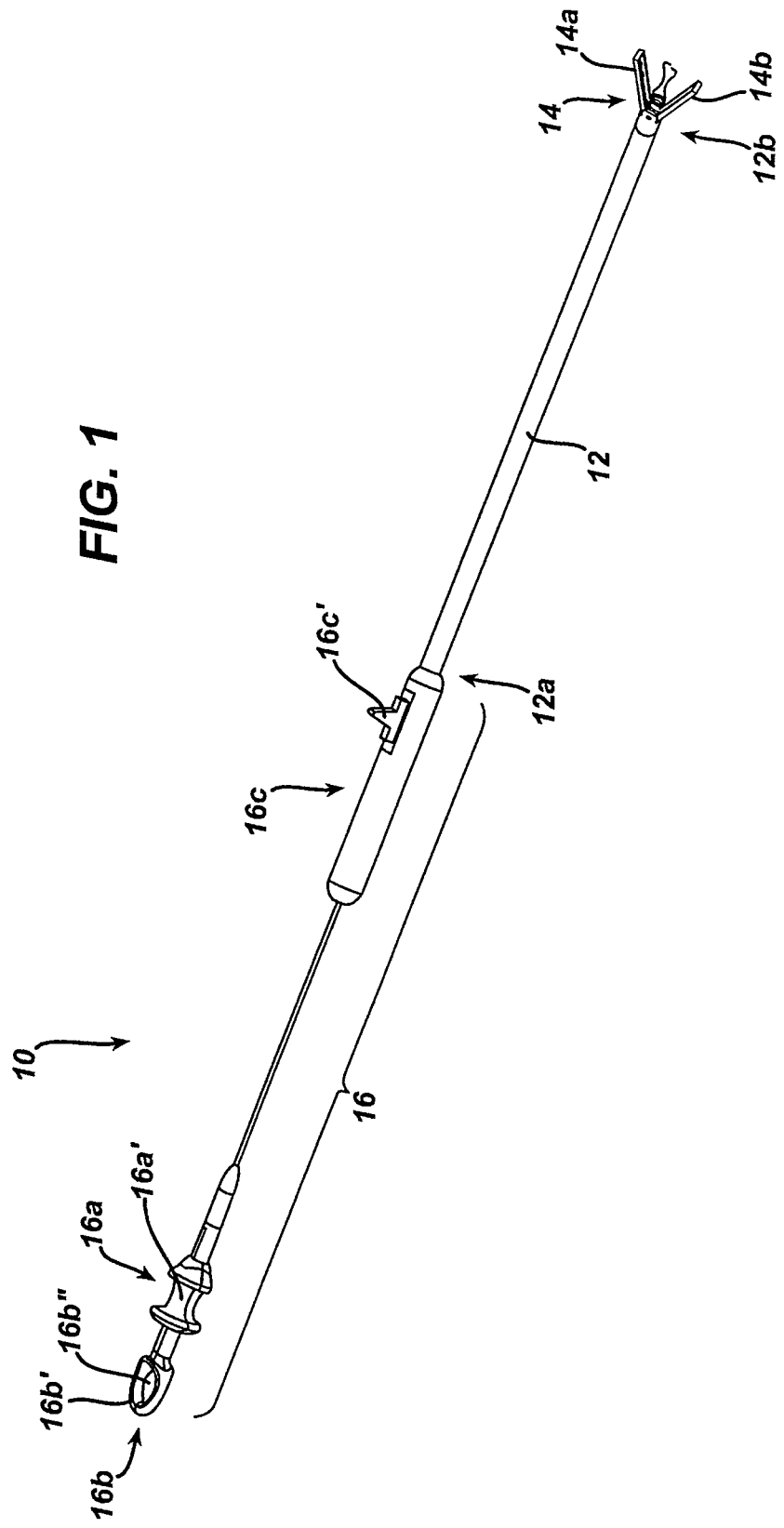
FIG. 1 is a perspective view of one embodiment of a device for applying an implantable tissue fastener.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for approximating tissue. The methods and devices utilize a device for applying an implantable tissue fastener and a variety of implantable tissue fasteners. The tissue-fastening device can be delivered endoscopically and can be adapted to function along side of or in conjunction with a flexible endoscope. In general, the device can include a flexible shaft having an implantable tissue fastener applier mechanism disposed at a distal end thereof and a handle for operating the implantable tissue fastener applier mechanism disposed at a proximal end thereof. For example, in an exemplary embodiment, the device can have a flexible elongate sheath, a handle that can be disposed at a proximal end of the elongate sheath, and an applier mechanism that can be disposed at a distal end of the elongate sheath and can be adapted to retain a tissue fastener. At least one actuator mechanism that can be disposed on the handle for actuating various operations of the device. For example, an actuator mechanism can be operatively associated with the applier mechanism such that actuating the actuator mechanism is effective to release the tissue fastener and thereby apply the tissue fastener to a targeted tissue. Although the device is shown and described for endoscopic use, one skilled in the art will appreciate that device could include a rigid shaft for laproscopic use.

FIGS. 1-4 illustrate one exemplary embodiment of a device 10 for applying an implantable tissue fastener. As indicated above, the device can generally include an elongate sheath 12 having an implantable tissue applier mechanism 14 disposed at a distal end 12b thereof and a handle 16 for operating the implantable tissue applier mechanism 14 at a proximal end 12a thereof. The implantable tissue applier 14 can have a variety of configurations, but in one exemplary embodiment, shown in FIGS. 1-4, the tissue applier mechanism 14 takes the form of first and second movable members or jaws 14a, 14b that are pivotably coupled to the distal end 12b of the elongate sheath 12 and are adapted to releasably retain a tissue fastener. The applier mechanism 14 can have a variety of shapes and sizes, but can generally be sized and shaped such that it can function along side of or in conjunction with a flexible endoscope. For example, the applier mechanism 14 can be sized and shaped such that the device 10 can be inserted through a working channel of endoscope, through an accessory channel that is mated to endoscope, or along a guide wire under endoscopic visualization.

Figure 2:
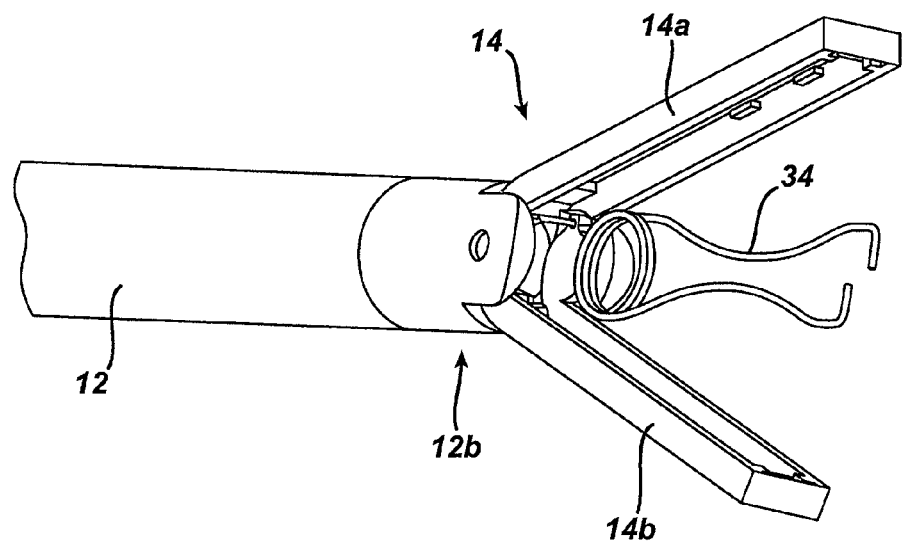
FIG. 2 is a perspective view of the distal end of the device shown in FIG. 1 showing one embodiment of an implantable tissue fastener disposed therein.
Figure 3:
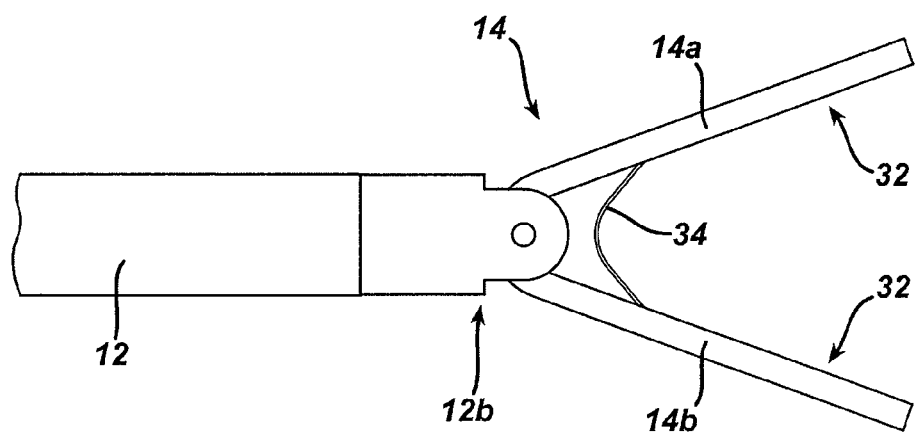
FIG. 3 is a perspective view of the distal end of the device shown in FIG. 1 showing another embodiment of an implantable tissue fastener disposed therein.
Figure 4:
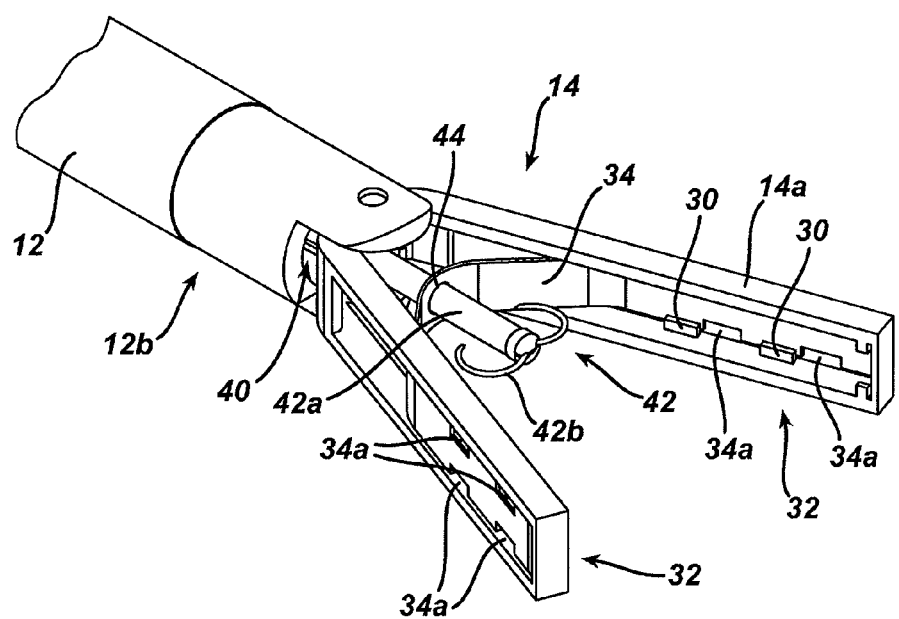
FIG. 4 is a perspective view of the distal end of the device shown in FIG. 3 showing a tissue grasping member extending from the device.

The applier mechanism 14 is shown in more detail in FIGS. 2-4. As shown, the mechanism 14 includes first and second members 14a, 14b. One or both of the first and second members 14a, 14b can be movable, and the jaw formed by the first and second members 14a, 14b can be adapted to pivot between open and closed positions. The movable jaw can be adapted to retain a tissue fastener in a tissue grasping condition and a natural condition in the open and closed positions, respectively. The movable jaw can be in the closed position as the device is inserted and advanced to a treatment site. Once the device is positioned adjacent the targeted tissue, the first and second members 14a, 14b can be pivoted from the closed position to the open position to allow the movable jaw to be positioned around the targeted tissue.

FIGS. 2-4 show the applier mechanism 14 in the open or tissue grasping position. As indicated above, the applier mechanism 14 can be adapted to retain a tissue fastener in both a natural condition and a tissue grasping condition. While the applier mechanism 14 can employ a variety of techniques to retain the tissue fastener, in an exemplary embodiment, shown in FIGS. 3 and 4, the first and second members 14a, 14b have tabs 30 that are disposed on an inner facing surface thereof 32 and are adapted to secure a tissue fastener 34 to the jaws. As shown, the tissue fastener 34 includes complementary shaped slots 34a that are cut therein and are adapted to align with the tabs 30 disposed on the jaws to allow the fastener 34 to be released from the device 10. In use, a tissue fastener 34 can be disposed in the jaws such that the slots 34a cut therein are not aligned with the tabs 30 disposed on the first and second members 14a, 14b. To release the fastener 34, a force can be applied to move the fastener 34 with respect to the first and second members 14a, 14b until the slots 34a are aligned with the tabs 30 thereby releasing the tissue fastener 34 from the jaws. In one embodiment, the force can be applied by the targeted tissue as it is retracted between the first and second members 14a, 14b of the jaws. In another exemplary embodiment, the fastener 34 can be stationary with respect to the jaws and the tabs 30 can be movable. In such a configuration, the tabs 30 can be advanced proximally or distally to align with the slots 34a in the fastener 34 and thereby release the fastener 34. In yet another embodiment, the tabs 30 can be entirely retractable to allow the fastener 34 to be released. In this embodiment, the tissue fastener need not have slots cut therein.

The applier mechanism can also have a tissue grasping member 42 associated therewith. FIG. 4 illustrates an exemplary embodiment of a tissue grasping member 42 that is slidably disposed in a longitudinally extending channel 40 that is formed in the device 10. The tissue grasping member 42 can have a variety of configurations. For example, as shown in FIG. 4, the tissue grasping member 42 can be a flexible elongate member 42a that includes a double hook 42b disposed at its distal end. Other exemplary embodiments for the distal end of the tissue grasping member include, but are not limited to, a single hook, an anvil, needle, corkscrew, or clamping mechanism. As shown, the tissue grasping member 42 extends distally from the flexible elongate sheath 12 and through an opening 44 formed in the tissue fastener 34 that is disposed between the first and second members 14a, 14b of the applier mechanism 14. The tissue grasping member 42 need not extend through the tissue fastener 34. For example, in another exemplary embodiment the grasping member can extend along side a fastener that is disposed in the applier mechanism. The tissue grasping member 42 can be advanced distally to engage or grasp the targeted tissue. Once the targeted tissue is engaged, the grasping member 42 can be retracted proximally to reconfigure and reposition the tissue between the first and second members 14a, 14b of the applier mechanism 14. Although the tissue grasping member 42 is shown and described as extending through a channel 40 that is formed in the flexible elongate sheath 12 of the device, one skilled in the art will appreciate that the tissue grasping member can be separate from the applier device. For example, in an exemplary embodiment, the tissue grasping member can be a separate device that is inserted through a different working channel of the endoscope or through an accessory channel that is mated to the endoscope.

The handle portion 16 of the device can have a variety of configurations but is generally positioned at a proximal portion 12a of the elongate sheath 12 and is configured to operate the applier mechanism 14 described above. In one exemplary embodiment, the handle 16 can include one or more actuator mechanisms for actuating various operations of the tissue approximating procedure. As shown in FIG. 1, the device includes an actuator mechanism 16a for moving the at least one movable member of the applier mechanism 14 between open and closed positions and an actuator mechanism 16b for advancing and retracting the tissue grasping member 42. As illustrated, the actuator mechanism 16a for moving the first and second members 14a, 14b can take the form of a trigger 16a' that is disposed on the handle portion 16 of the device 10. Applying a force to the trigger 16a' can be effective to cause the first and second members 14a, 14b to pivot between open and closed positions. Referring back to FIG. 1, the actuator mechanism 16b for operating the tissue grasping member 42 can take the form of a pull knob 16b' that is adapted to advance and/or retract the grasping member 42 upon actuation. The pull knob 16b' can be operatively associated with the tissue grasping member 42 such that applying a force to the knob 16b' is effective to slidably move the grasping member 42 with respect to the device 10. As shown, the grasping member actuator mechanism 16b includes a cutout 16b'' to allow the user to grasp the pull knob 16b'. As indicated above, the tissue grasping member 42 can retract the targeted tissue into the jaws of the applier mechanism 14 such that the tissue applies a force to the tissue fastener to cause the fastener to be released from the jaws. Although the device 10 is shown and described as having two separate actuator mechanisms 16a, 16b, one skilled in the art will appreciate that a variety of combinations and configurations of actuator mechanisms can be used to carry out the operations of the tissue approximating procedure. For example, in another exemplary embodiment, where the tissue fastener is not self-deploying, the device 10 can include an additional actuator mechanism for deploying an implantable tissue fastener 34 that is retained by the applier mechanism 14.

A variety of implantable tissue fasteners can be used with the tissue fastener applier device 10 described above. For example, as shown in FIGS. 5-10B, the implantable tissue fastener generally includes a central body portion, a first anchor arm, and a second anchor arm. The first anchor arm can extend from a first end of the central body portion and can have a terminal end that is opposite the first end of the central body portion. The second anchor arm can extend from a second end of the central body portion and can have a terminal end that is opposite the second end of the central body portion. The terminal ends of the first and second anchor arms can be biased towards each other such that terminal ends are in close proximity with each other, or overlapping, when the tissue fastener is in a natural condition (i.e., when no force is being applied to the tissue fastener).

Figure 5:
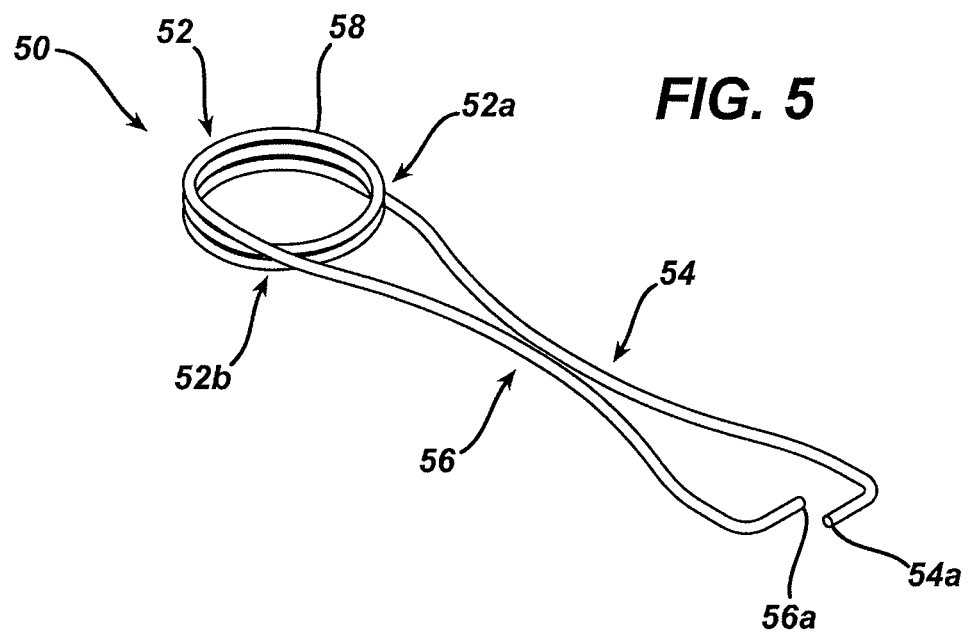
FIG. 5 is a perspective view of one embodiment of an implantable tissue fastener.

FIG. 5 illustrates one exemplary embodiment of a tissue fastener 50 having a central body portion 52 and first and second anchor arms 54, 56. The central body portion 52 of the tissue fastener can have a variety of configurations. For example, as shown, the central body portion takes the form of a torsional spring 58. The spring 58 can be adapted to deliver a sufficient torque energy to allow the first and second anchor arms 54, 56 to apply an approximate compressive force to the targeted tissue of up to about 7.5 lbf. The central body portion 52 can be formed from a variety of materials including, but not limited to, stainless steel, titanium, and super elastic alloys such as a nickel titanium alloy. Where the central body portion 52 is formed from a super elastic alloy, the central body portion 52 need not take the form of a spring (FIGS. 7-10B) as the super elastic alloy can allow the central body 52 to deliver a similar torque energy without the spring structure. The central body portion 52 and the first and second anchor arms 54, 56 can be formed entirely of a single material or can be formed from any combination of materials. For example, in an exemplary embodiment, the first and second anchor arms 54, 56 can be formed from stainless steel and the central body portion 52 can be formed from a super elastic alloy. The materials can also be selected such that the fastener 50 can be used as a marker when deployed in a target tissue.

A variety of configurations are also available for the first and second anchor arms 54, 56. In general, the first and second anchor arms can extend from the central body portion to form a substantially U-shaped or V-shaped fastener. In one exemplary embodiment, shown in FIG. 5, the central body portion 52 and the first and second anchor arms 54, 56 are part of a unitary structure. In another embodiment, the central body portion can be a separate element that is coupled to the first and second anchor arms. The first and second anchor arms 54, 56 can have a variety of shapes and sizes. For example, as shown in FIG. 5, the anchor arms 54, 56 have an arcuate shape. Such a configuration can allow the arcuate portion of the anchor arms 54, 56 to engage and apply a compression force to the targeted tissue. In another embodiment, the anchor arms can be substantially straight. As illustrated, one arm is greater in length than the other such that the terminal ends 54a, 56a of the first and second anchor arms are staggered. However, in another exemplary embodiment, the first and second anchor arms can be equal in length.

As shown in FIG. 5, the first and second anchor arms 54, 56 extend from first and second ends 52a, 52b of the central body portion 52 and each have a terminal end 54a, 56a that is opposite the first and second ends 52a, 52b of the central portion 52, respectively. The terminal ends 54a, 56a of the anchor arms 54, 56 can be biased towards to each other such that the terminal ends 54a, 56a are in close proximity, or overlapping, when the tissue fastener 50 is in a natural condition. A variety of configurations are available for the terminal ends 54a, 56a of the first and second anchor members 54, 56. For example, in one embodiment, the terminal ends 54a, 56a can be blunt or rounded, as it is not necessary for the terminal ends 54a, 56a to penetrate the target tissue. Alternatively, the terminal ends can include piercing points that are adapted to penetrate tissue. The piercing points can extend along the axis of the first and second anchor arms or can extend at angle with respect to the axis of the arm. In yet another embodiment, the terminal ends of the first and second anchor arms can include mating elements that are adapted to lock the tissue fastener in a closed position when it is deployed in a target tissue. While a variety of mating elements can be used, in one exemplary embodiment, the terminal end of the first anchor arm can be received by a recess formed in the terminal end of the second anchor arm and be secured by interference fit or my mechanism interlock.

Figure 6:
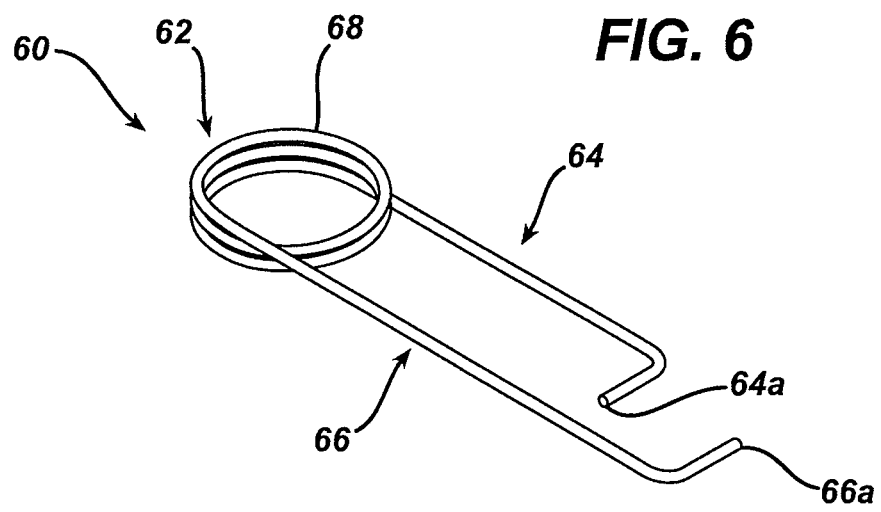
FIG. 6 is a perspective view of another embodiment of an implantable tissue fastener.

FIG. 6 illustrates another exemplary embodiment of a tissue fastener 60 having a central body portion 62 and first and second anchor arms 64, 66. Similar to the embodiment shown in FIG. 5, the central body portion 62 takes the form of a torsional spring 68 and the first and second anchor arms 64, 66 differ in length such that the terminal ends 64a, 66a of the anchor arms 64, 66 are staggered. However, in this embodiment, instead of having an arcuate shape, the first and second anchor arms 64, 66 are straight.

Figure 7:
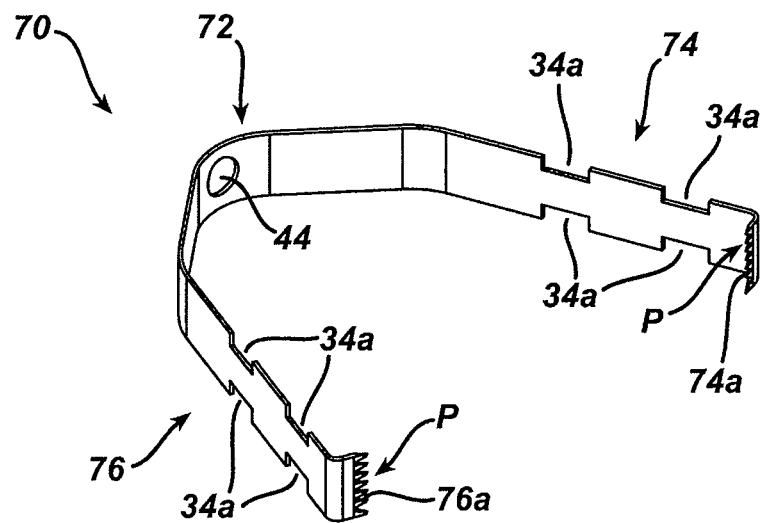
FIG. 7 is a perspective view of another embodiment of an implantable tissue fastener.

Another exemplary embodiment of a tissue fastener 70 is shown in FIG. 7. As shown, the fastener 70 has a central body portion 72 and first and second anchor arms 74, 76. Unlike the embodiments described above, the central body portion 72 is not in the form of a spring but is, instead, a substantially U-shaped member that can be formed from a super elastic alloy. As described above, the fastener 70 can include slots 34a that are cut therein and are adapted to align with tabs disposed on the applier jaws to allow the fastener 70 to be released from the device 10. The fastener 70 can include an additional opening or cutout 44 that is formed in the central body portion 72 and can be configured to allow a tissue grasping member to extend therethrough in use. As shown, the fastener 70 further includes piercing points P extend at angle with respect to the axes of the first and second arms 74, 76 and are in the form of a plurality of teeth that are disposed on the terminal ends 74a, 76a thereof.

Figure 8:
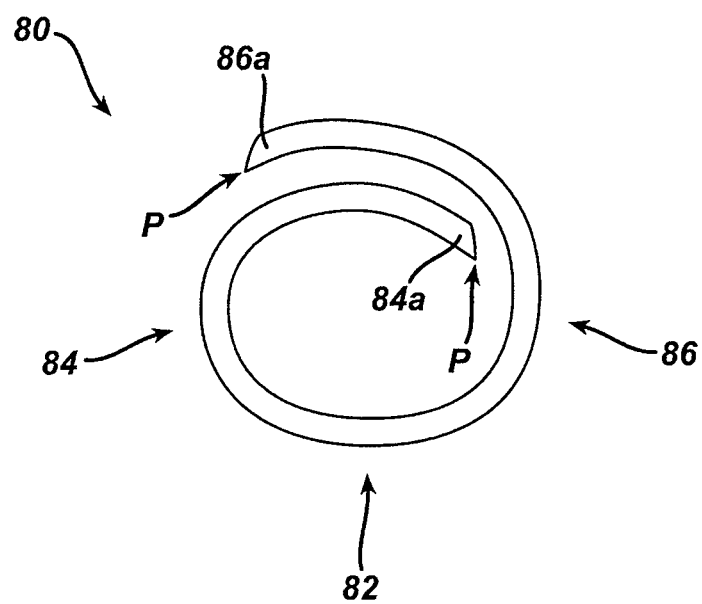
FIG. 8 is a perspective view of another embodiment of an implantable tissue fastener.

FIG. 8 illustrates another exemplary embodiment of a tissue fastener 80 wherein the central body portion 82 and first and second anchor arms 84, 86 are curved such that they form a fastener 80 having one continuous curve. As shown, the terminal ends 84a, 86a of the curved first and second anchor arms 84, 86 overlap forming a substantially circular-shaped fastener when the fastener is in a natural condition. The fastener 80 also includes piercing points P that extend along the curve of the first and second arms 84, 86 and are in the form of terminal ends 84a, 86a that are sharp or pointed.

Figure 9A:
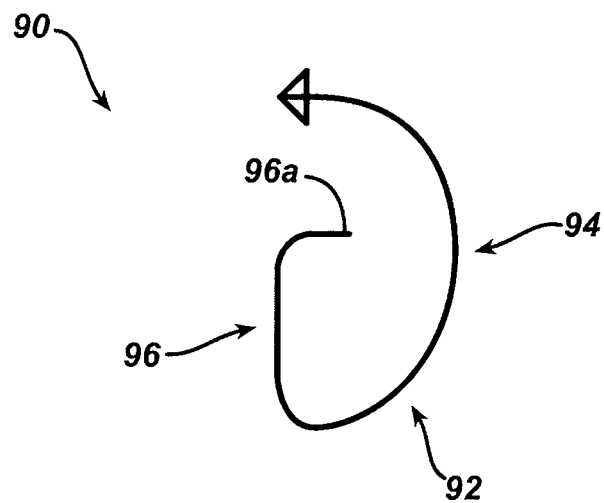
FIG. 9A is a perspective view of another embodiment of an implantable tissue fastener.
Figure 9B:
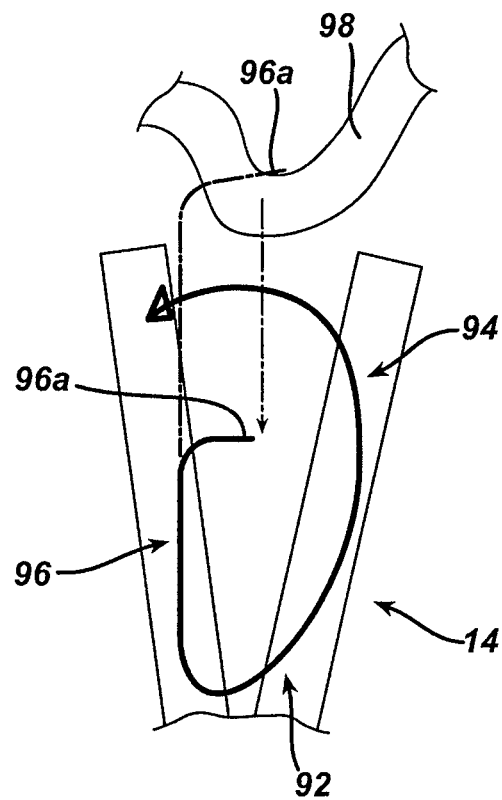
FIG. 9B is a perspective view of the implantable tissue fastener shown in FIG. 9A in use.

FIGS. 9A-9B illustrate another exemplary embodiment of a tissue fastener 90 having a curved central body portion 92. Similar to the embodiment shown in FIG. 8, a first anchor arm 94 can be curved and can extend from the curved central body portion 92 such that it continues along the same curve. The second anchor arm 96, however, can be straight and can include a terminal end 96a that extends perpendicular thereto. Such a configuration can allow the terminal end 96a of the second anchor arm 96 to function as a tissue grasping member. As shown in FIG. 9B, the terminal end 96a of the second anchor arm 96 engages the target tissue 98 to draw it into the jaws of the applier mechanism 14 before the fastener 90 is deployed.

Figure 10A:
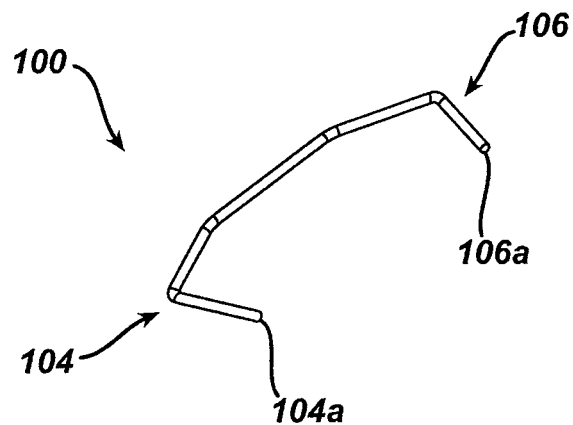
FIG. 10A is a perspective view of one embodiment of an implantable tissue fastener.
Figure 10B:
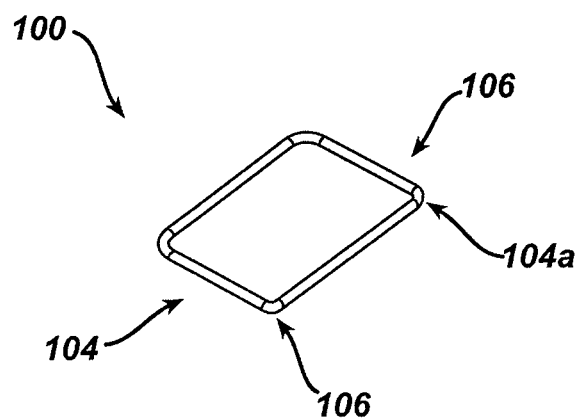
FIG. 10B is a perspective view of the implantable tissue fastener shown in FIG. 10A in an engaged position.

FIGS. 10A-10B illustrate yet another exemplary embodiment of a tissue fastener 100. Similar to several of the embodiments described above, the tissue fastener 100 is generally U-shaped in its tissue grasping condition (FIG. 10A) and includes first and second anchor arms 104, 106 that are straight. In its natural condition (FIG. 10B), however, the terminal ends 104a, 106a of the first and second anchor arms 104, 106 wrap around to form a generally rectangular-shaped fastener that resembles a box staple.

Figure 11A:
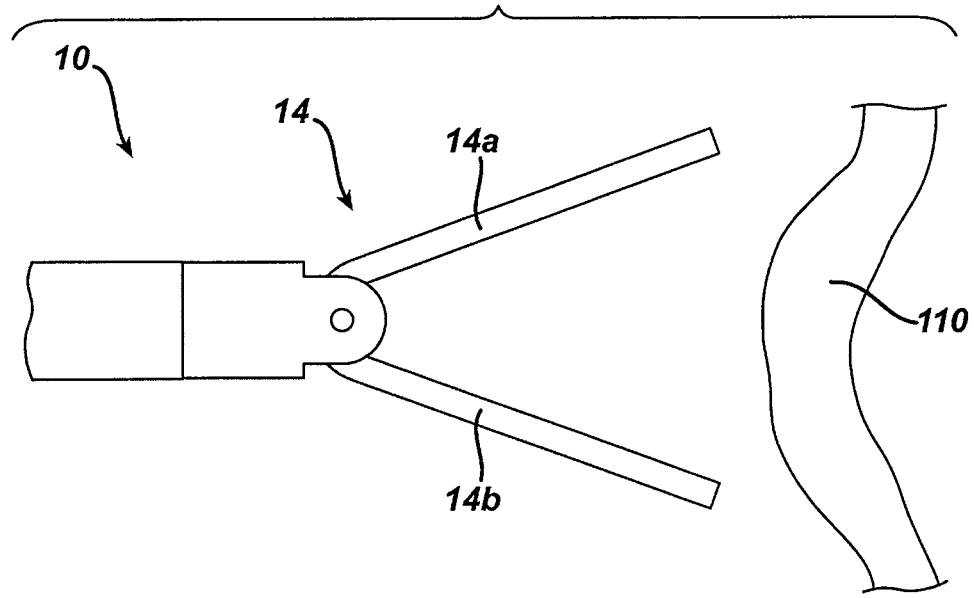
FIG. 11A is a perspective view of one embodiment of a device for applying an implantable tissue fastener positioned adjacent a target tissue.

The present invention also provides methods of approximating a target region of tissue. The method can include inserting to a target site a device for applying an implantable tissue fastener. The device can be used in conjunction with an endoscope to facilitate viewing of at least a portion of the method for approximating and can be inserted through a working channel of the endoscope, through an accessory channel that is mated to the endoscope, or inserted translumenally along a guide wire under direct endoscopic vision. The approximating device can take the form of any of the embodiments described above but can generally include a flexible elongate sheath, a handle that can be disposed at a proximal end of the elongate sheath, and an applier mechanism that can be disposed at a distal end of the elongate sheath and can be adapted to releasably retain a tissue fastener. FIGS. 11A-11D illustrate one exemplary embodiment of approximating a target region of tissue. As shown in FIG. 11A, the approximating device 10 is positioned adjacent the target tissue 110 of an internal organ such as the stomach. Once the device 10 is positioned adjacent the target tissue 110, the device 10 can be actuated to pivot the first and second movable members 14a, 14b of the applier mechanism 14 from a closed to an open position and move the tissue fastener from its natural condition to a tissue grasping condition.

Figure 11B:
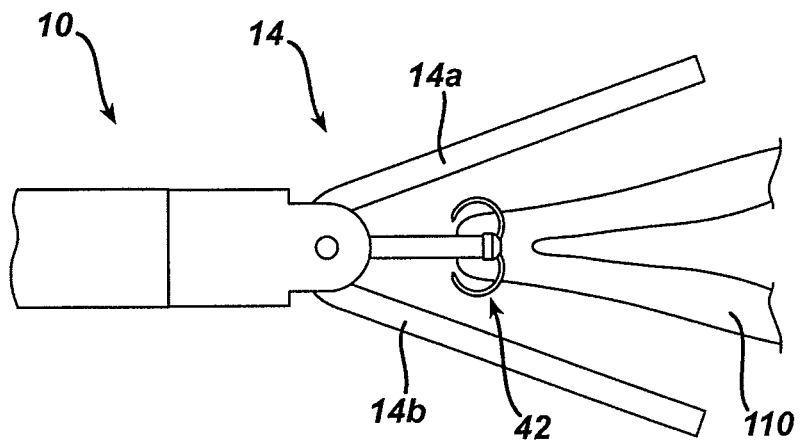
FIG. 11B is a perspective view of one embodiment of a device for applying an implantable tissue fastener positioned adjacent a target tissue showing a tissue grasping member engaging and reconfiguring a target tissue.
Figure 11C:
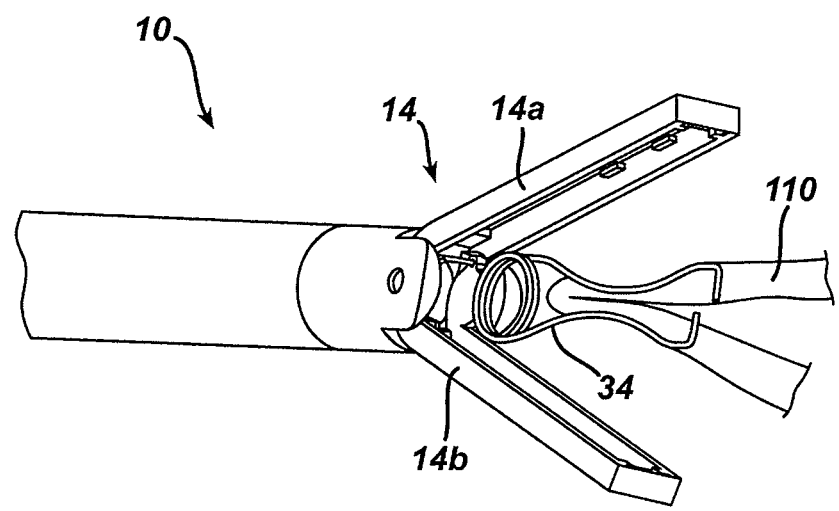
FIG. 11C is a perspective view of one embodiment of a device for applying an implantable tissue fastener releasing a tissue fastener to approximate a target tissue.

The target tissue can then be reconfigured in a desired orientation. Reconfiguring the targeted tissue can include engaging and manipulating an inner surface of the targeted tissue to change the shape of the targeted tissue. The reconfigured tissue can take a variety of shapes including, for example, a fold, a bulge, a mound, a plication, a ridge, a tube, a cone, and a horn. FIG. 11B shows the target tissue 110 being reconfigured or manipulated by a tissue grasping member 42 that is slidably disposed in a longitudinally extending channel formed in the device 10.

After manipulating the tissue to draw the tissue into the jaws of the applier mechanism 14 and reconfigure the tissue 110 in a desired orientation, the device 10 can be actuated to deploy a tissue fastener 34 the target tissue 110 to secure the tissue 110 in the reconfigured orientation. Prior to release, the fastener 34 is retained by the applier mechanism 14 in a tissue grasping condition such that upon deployment or release from the applier 14 jaws the fastener 34 will revert to its natural condition or unconstrained shape to engage and secure the reconfigured tissue 110. Following deployment of the fastener 34, the jaws of the applier mechanism 14 can be pivoted to a closed position to applying clamping force to the tissue fastener 34. Although not necessary as the fastener is self-deploying, it may be desirable to apply a clamping force to secure any mating elements that are disposed on the terminal ends of the first and second anchor arms of the fastener.

Figure 11D:
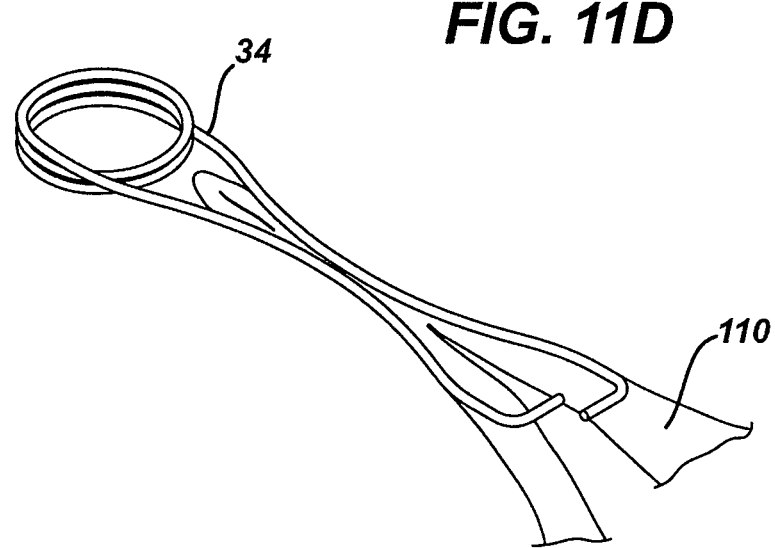
FIG. 11D is a perspective view of one embodiment of an implantable tissue fastener deployed in a target tissue.

The steps of actuating the device to move the tissue fastener from its natural condition to a tissue grasping condition, reconfiguring the target tissue, and actuating the device to deploy a tissue fastener can be repeated as needed. Once the target tissue is reconfigured and secured as desired, the first and second movable members of the applier mechanism can be pivoted to a closed position and the device can be removed from the treatment site. FIG. 11D shows an exemplary embodiment of a reconfigured target tissue 110 secured by a fastener 34 following the removal of the device 10.

A person skilled in the art will appreciate that the present invention has application in conventional endoscopic and open surgical instrumentation as well application in robotic-assisted surgery.

The devices disclosed herein, and particularly the applier device, can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for applying a fastener to tissue, comprising:
    inserting to a target site a device for applying an implantable tissue fastener disposed in the device with at least one slot formed in the tissue fastener not being aligned with at least one tab formed on the device, the device having associated therewith jaws adapted to retain and release the tissue fastener in its natural condition;

positioning the device adjacent the targeted tissue;

pivoting the jaws from a closed position to an open position to move the tissue fastener from its natural condition to a tissue grasping condition, the at least one slot formed in the tissue fastener not being aligned with the at least one tab formed on the device when the jaws are in the closed and open positions and when the tissue fastener is in the tissue grasping condition;

reconfiguring the targeted tissue; and with the jaws in the open position and with the tissue fastener in the tissue grasping condition, moving the at least one tab relative to the tissue fastener to release the tissue fastener to approximate the targeted tissue by disengaging the tissue fastener from the at least one tab formed on the device, wherein releasing the tissue fastener to approximate the targeted tissue comprises aligning the at least one tab with the at least one slot formed in the tissue fastener such that, with the jaws in the open position and with the tissue fastener in the tissue grasping condition, the at least one tab moves through an opening defined by the at least one slot.

2. The method of claim 1, wherein moving the jaws comprises actuating an actuator mechanism disposed on a handle of the device to move the jaws from the closed to the open position.

3. The method of claim 1, further comprising actuating the device to move the jaws from the open to the closed position to apply a clamping force to the tissue fastener.

4. The method of claim 1, wherein reconfiguring the targeted tissue comprises retracting the tissue to position the tissue adjacent the jaws.

5. The method of claim 4, wherein retracting the tissue is effective to release the tissue fastener.

6. The method of claim 1, wherein reconfiguring the targeted tissue comprises manipulating the tissue with a tissue grasping member.

7. The method of claim 6, wherein the tissue grasping member is slidably disposed in a longitudinally extending channel formed in the device.

8. The method of claim 6, wherein the tissue grasping member is a separate device.

9. The method of claim 6, wherein manipulating the tissue with the tissue grasping member comprises actuating an actuator mechanism disposed on a handle of the device to move the tissue grasping member distally with respect to the device and into engagement with the targeted tissue.

10. The method of claim 1, wherein reconfiguring the targeted tissue comprises manipulating the tissue to be in the shape selected from the group consisting of a plication, a bulge, a flap, a tube, and a cone.

11. The method of claim 1, further comprising repeating the steps of pivoting the jaws to move the tissue fastener from its natural condition to a tissue grasping condition, reconfiguring the targeted tissue, and releasing the tissue fastener to approximate the targeted tissue.

12. The method of claim 1, wherein reconfiguring and approximating the targeted tissue are performed using only the device for applying an implantable tissue fastener.

13. The method of claim 1, further comprising endoscopically viewing at least a portion of the method for applying the fastener.

14. The method of claim 1, wherein inserting the device comprises inserting the device translumenally.

15. The method of claim 1, wherein inserting the device comprises inserting the device laparoscopically.

16. The method of claim 1, wherein inserting the device for applying an implantable tissue fastener comprises inserting the device through a working channel of an endoscope.

17. The method of claim 1, wherein inserting the device for applying an implantable tissue fastener comprises inserting the device through an accessory channel mated to an endoscope.

18. The method of claim 1, wherein the targeted tissue is an internal organ that is endoscopically accessed.

19. The method of claim 1, wherein the tissue fastener comprises a central body portion formed from a super elastic alloy.

20. The method of claim 1, wherein the targeted tissue is approximated by penetrating the targeted tissue with piercing points disposed on the tissue fastener.

21. The method of claim 1, wherein moving the at least one tab relative to the tissue fastener comprises retracting the at least one tab relative to the tissue fastener.

22. The method of claim 1, wherein the at least one slot and the at least one tab have complementary shapes such that releasing the tissue fastener to approximate the targeted tissue comprises aligning the at least one slot with the at least one tab to move the at least one tab through the at least one slot.

23. A method for applying a fastener to tissue, comprising:

inserting to a target site a device for applying an implantable tissue fastener disposed in the device with at least one slot formed in the tissue fastener not being aligned with at least one tab formed on the device, the device having associated therewith jaws adapted to retain and release the tissue fastener in its natural condition;

positioning the device adjacent the targeted tissue;

pivoting the jaws from a closed position to an open position to move the tissue fastener from its natural condition to a tissue grasping condition, the at least one slot formed in the tissue fastener not being aligned with the at least one tab formed on the device when the jaws are in the closed and open positions and when the tissue fastener is in the tissue grasping condition;

reconfiguring the targeted tissue; and with the jaws member in the open position and with the tissue fastener in the tissue grasping condition, moving the tissue fastener relative to the at least one tab to release the tissue fastener to approximate the targeted tissue by disengaging the tissue fastener from the at least one tab formed on the device, wherein releasing the tissue fastener to approximate the targeted tissue comprises aligning the at least one tab with the at least one slot formed in the tissue fastener such that, with the jaws in the open position and with the tissue fastener in the tissue grasping condition, the at least one tab moves through an opening defined by the at least one slot.

24. The method of claim 23, wherein moving the tissue fastener relative to the at least one tab comprises longitudinally sliding the tissue fastener through the device.

* * * * *